United States Patent [19]

Bardi et al.

[11] Patent Number: 5,635,721
[45] Date of Patent: Jun. 3, 1997

[54] APPARATUS FOR THE LINER ACCELERATION OF ELECTRONS, PARTICULARLY FOR INTRAOPERATIVE RADIATION THERAPY

[75] Inventors: Gianluca Bardi, Florence; Mario Fantini; Sandro Sandri, both of Rome; Felice Santoni, Grotte Santo Stefano, all of Italy

[73] Assignee: Hitesys S.p.A., Aprilia, Italy

[21] Appl. No.: 528,965

[22] Filed: Sep. 15, 1995

[30] Foreign Application Priority Data

Sep. 19, 1994 [IT] Italy .................. LT94A0012

[51] Int. Cl.$^6$ ................ H01J 33/00; H05H 9/00
[52] U.S. Cl. ................ 250/492.3; 600/1; 600/2; 378/64; 378/65; 315/5.41; 315/5.42
[58] Field of Search .................. 250/492.3; 600/1, 600/2; 378/64, 65; 315/5.41, 5.42

[56] References Cited

U.S. PATENT DOCUMENTS 3,796,906  3/1974  Henry-Bezy et al. ............ 315/5.41

5,321,271  6/1994  Schonberg et al. ............... 250/492.3

*Primary Examiner*—Jack I. Berman
*Attorney, Agent, or Firm*—Guido Modiano; Albert Josif

[57] ABSTRACT

An apparatus for the linear acceleration of electrons, particularly for intraoperative radiation therapy, including:

an articulated structure for moving a radiating head that comprises an acceleration structure constituted by a plurality of cavities;

a modulator for generating, controlling, and transmitting a radio-frequency to the cavities of the acceleration structure; and processing and control devices adapted to control the apparatus; the modulator is separate from the radiating head and the connection occurs by virtue of waveguide means adapted to carry the radio-frequency to the acceleration structure.

12 Claims, 5 Drawing Sheets

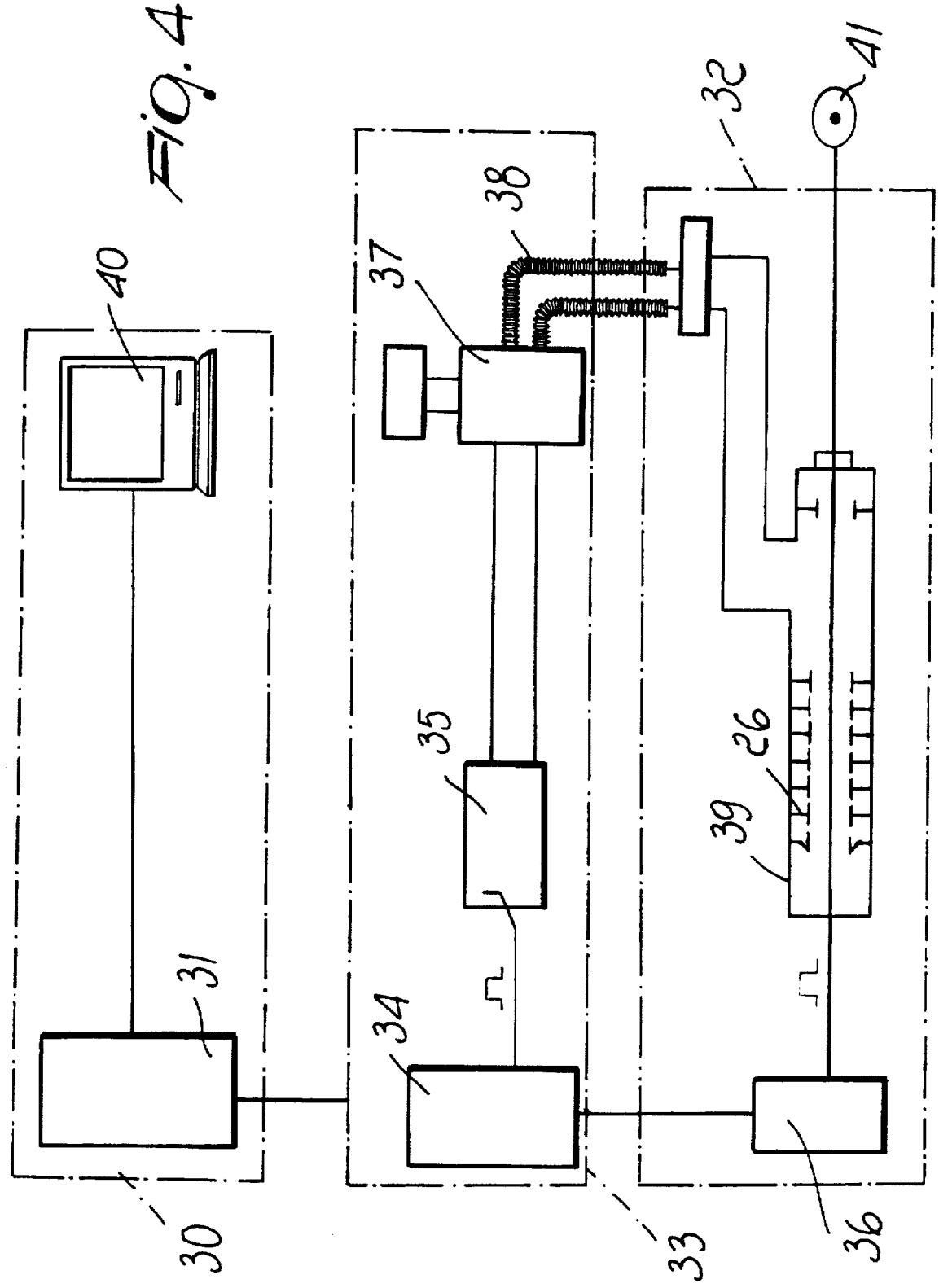

APPARATUS FOR THE LINER ACCELERATION OF ELECTRONS, PARTICULARLY FOR INTRAOPERATIVE RADIATION THERAPY

BACKGROUND OF THE INVENTION

The present invention relates to an apparatus for the linear acceleration of electrons, particularly for intraoperative radiation therapy.

Intraoperative radiation therapy is a therapeutic method used in treating deep neoplasms and consists in delivering a single intense dose of radiation onto a tumoral mass, preventing the dose from affecting the surrounding healthy tissues.

Its field of utilization ranges from surgically inoperable tumors, to tumoral residues after partial surgical exeresis, to a tumoral bed after full surgical removal. In this manner, by delivering the dose of radiation directly onto the tumor or onto the macroscopic or microscopic tumoral residue, it is possible to spare the peritumoral healthy tissues that are instead affected by radiation in conventional radiation therapy with external beams.

Currently there is growing interest in the use of this therapeutic method for a wide range of tumors, particularly those affecting the abdomen, the pelvis, and the chest. The association of this therapy with surgery and with conventional radiation therapy allows to considerably improve local control of advanced-phase neoplasms.

Large electron accelerators, which allow to treat a patient both with an electron beam and with X rays, have been successful in the execution of this intraoperative radiation therapy. Use of electron-bee therapy offers high versatility in treating tumoral residues after surgical removal as well as tumoral masses deemed inoperable.

However, large electron accelerators have some drawbacks which can limit their use.

A first drawback can be found in their high cost.

A second drawback is the considerable bulk of the apparatus.

The real drawback of electron accelerators, however, resides in the intense irradiation produced, which cannot be confined with simple movable panels, and therefore in the consequent need for heavily shielded work sites.

Special radiation-therapy bunkers are therefore built for this purpose with concrete walls one or two meters thick. The shielding of radiation-therapy sites is governed by specific safety regulations.

For intraoperative radiation therapy, the patients are transferred under anaesthesia from the operating room to the radiation-therapy bunker, under constant monitoring; the subsequent steps of the process and, usually, the final step of the surgery being performed on the patient take place in said bunker. Only in rare cases the operating rooms are located directly in a bunker so as to simultaneously act as a radiation-therapy room as well.

The need to transfer the patient to a location other than the operating room causes problems linked to the risks of transferring the patient under anaesthesia and to the time that elapses between surgical exeresis and subsequent radiation therapy.

It is furthermore necessary to strictly schedule each operation according to the availability of access to the radiation-therapy site, and this increases the working time requirements and reduces the number of patients who can utilize this radiation therapy.

Furthermore, in current electron accelerators the irradiation unit (known as "radiating head"), the modulator, and the components for therapy are assembled in a single block that is difficult to move due to its weight and size.

This does not allow the radiating head to be placed precisely in space and to be moved in a flexible manner, so that the electron beam treats the entire tumoral mass involved, despite the irregular shape that said mass may have.

In order to avoid this drawback, with the linear electron accelerators used so far it is necessary to increase the cross-section of the radiation beam, with greater problems in terms of shielding and damage to healthy surrounding tissues.

Finally, the difficulty in moving the radiating head makes it impossible to vary the dose of emitted radiation for each point of the tumoral mass, so as to administer the dose prescribed by the physician to each area.

SUMMARY OF THE INVENTION

A principal aim of the present invention is therefore to provide an apparatus for the linear acceleration of electrons, particularly for intraoperative radiation therapy, which can be used directly in the operating room without special radiation-protective measures.

Within the scope of this aim, an object of the present invention is to provide an apparatus for the linear acceleration of electrons that allows the flexible and precise movement in space of the electron beam to treat tumoral masses having variable and different shapes.

Another object of the present invention is to provide an apparatus for the linear acceleration of electrons that allows to provide the electron acceleration section separately from the radio-frequency generation and control section.

A further object of the present invention is to provide an apparatus for the linear acceleration of electrons that allows to achieve a very low X-ray level that can be easily shielded.

Another object of the present invention is to provide an apparatus for the linear acceleration of electrons that allows to spatially vary the dose of radiation that is incident to a given tumoral area.

Another object of the present invention is to provide an apparatus for the linear acceleration of electrons having a modest size and weight.

Another object of the present invention is to provide an apparatus for the linear acceleration of electrons that avoids the need for the external focusing and centering devices for the emitted electron beam that are present in prior-art accelerators.

Another object of the present invention is to provide an apparatus for the linear acceleration of electrons that allows to eliminate the cathode from the acceleration structure.

Another object of the present invention is to provide an apparatus for the linear acceleration of electrons that is highly reliable, relatively easy to manufacture, and at competitive costs.

This aim, these objects, and others which will become apparent hereinafter are achieved by an apparatus for the linear acceleration of electrons, particularly for intraoperative radiation therapy, characterized in that it comprises:

an articulated structure for moving irradiation means that comprise an acceleration structure constituted by a plurality of cavities;

modulation means for generating, controlling, and transmitting a radio-frequency to said cavities of said acceleration structure; and processing and control means adapted to control said apparatus, said modulation means being separate from said irradiation means, the connection occurring by virtue of waveguide means adapted to carry the radio-frequency to said acceleration structure.

BRIEF DESCRIPTION OF THE DRAWINGS

Further characteristics and advantages of the invention will become apparent from a preferred but not exclusive embodiment of the apparatus according to the invention, illustrated only by way of non-limitative example in the accompanying drawings, wherein:

FIG. 4 is a block diagram of an apparatus for the linear acceleration of electrons according to the invention;

DESCRIPTION OF THE PREFERRED EMBODIMENTS

Figure 1:
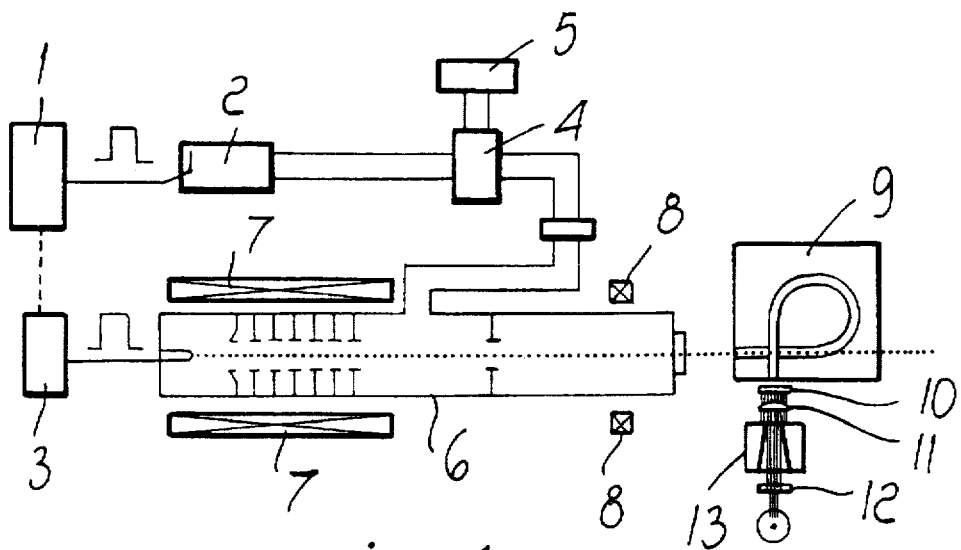
FIG. 1 is a view of a known type of apparatus for the linear acceleration of electrons.

With reference to FIG. 1, the known acceleration apparatus comprises a radio-frequency modulator 1, a magnetron 2, cathode modulation means 3, circulation means 4, a load of cooling water 5, an acceleration structure 6, a focusing magnet 7, a centering magnet 8, a deflector magnet 9, a beam diffuser 10, a beam equalizer 11, a beam applicator 12, and a beam collimator 13.

Figure 2:
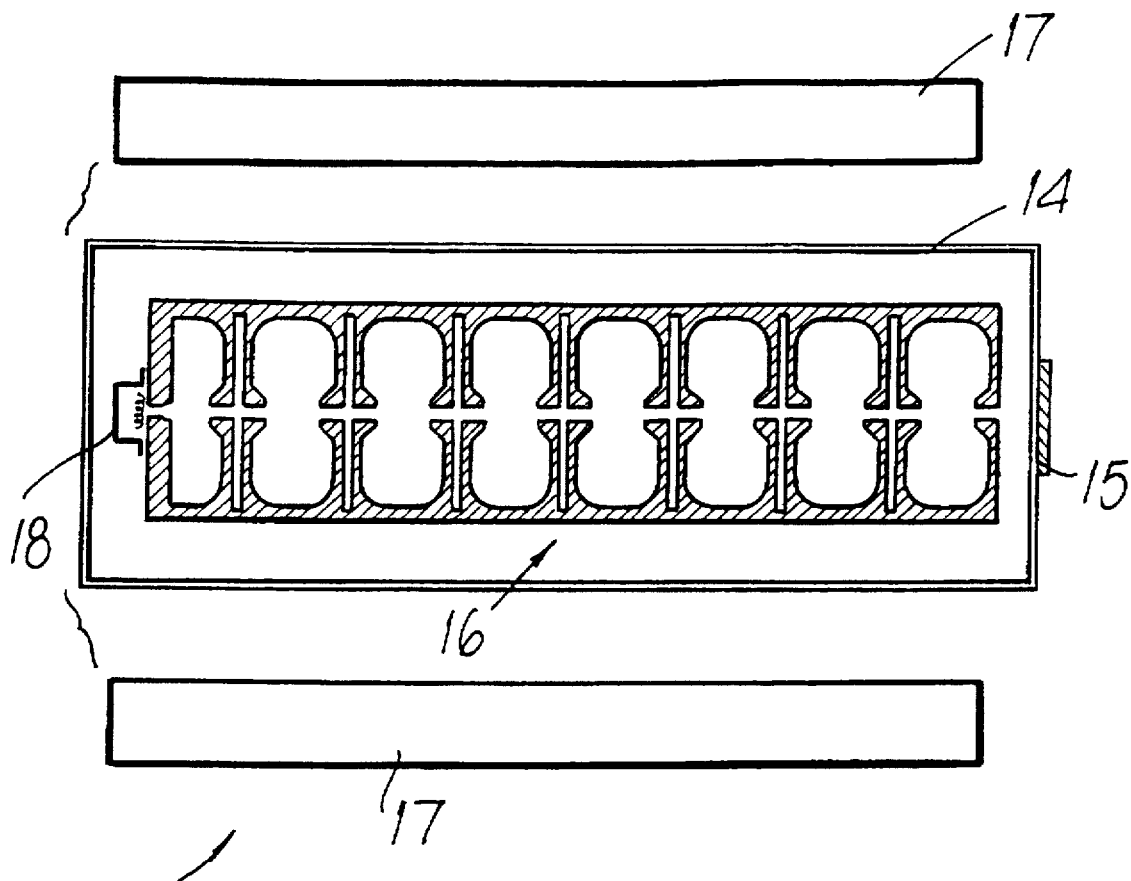
FIG. 2 is a view of the configuration of the acceleration cavities for a known type of acceleration apparatus.

FIG. 2 illustrates in detail the acceleration structure 16 of the acceleration apparatus of FIG. 1, which is constituted by a set of acceleration cavities 16, by a cathode 18 connected to the first acceleration cavity, and by a titanium plate 15 aligned with the axis of the last acceleration cavity.

The acceleration cavities 16 are enclosed by an external vacuum-tight jacket 14, and two magnets 17 are located outside said external jacket 14. The function of the two magnets is to induce the magnetic field strength that is required for the collimation of the electron beam along the axis of the acceleration structure.

Figure 5:
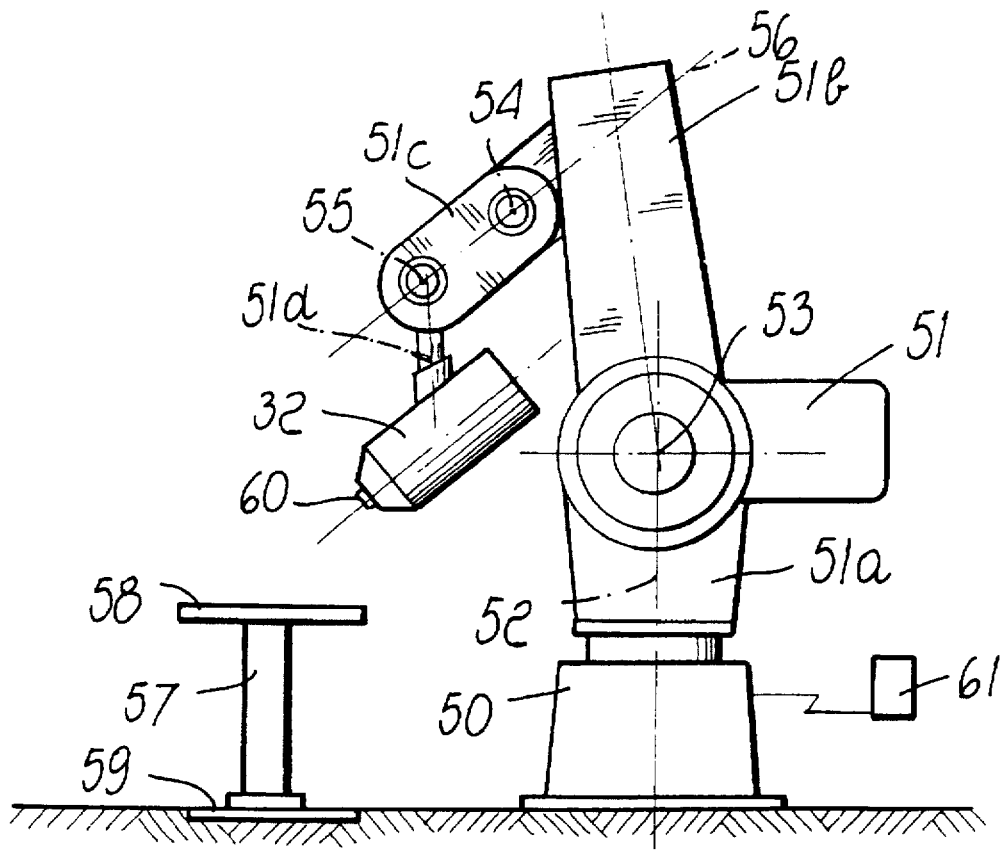
FIG. 5 is a lateral elevation view of a robot and of the radiating head connected thereto, said robot and said head being a part of the acceleration apparatus according to the invention.
Figure 3:
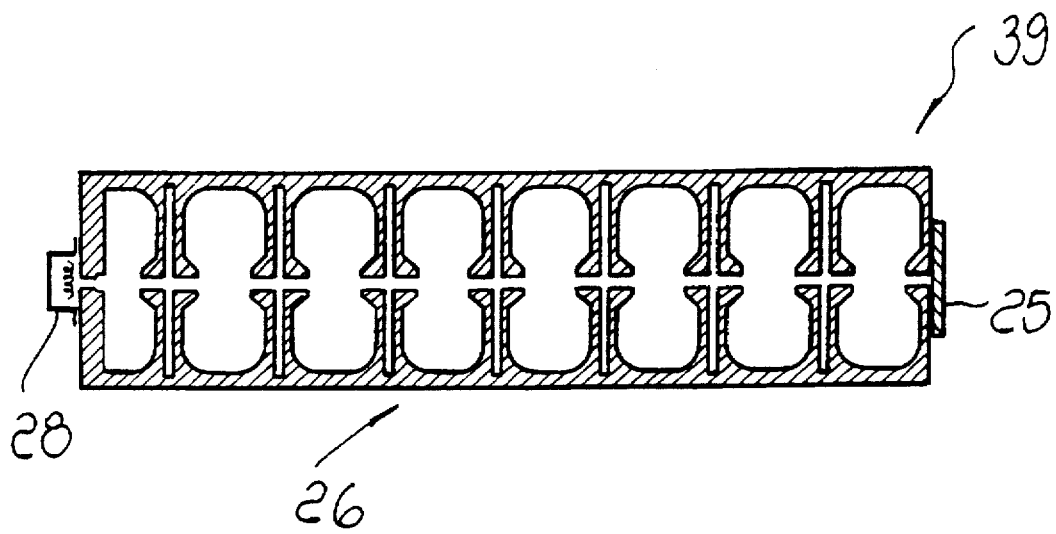
FIG. 3 is a view of the configuration of the acceleration cavities for an acceleration apparatus according to the invention.

With reference instead to FIGS. 3, 4, and 5, the acceleration apparatus according to the invention comprises control and processing means 30.

The control and processing means 30 comprise: power supply means 31; processing means 40, which advantageously comprise a computer; the cooling system of the apparatus; the means for distributing motive power; and the safety devices (not shown).

The control and processing means 30 are connected to modulation means 33 that comprise radio-frequency modulation means 34 connected to a magnetron 35 and to cathode modulation means 36. The magnetron 35 is protected from accidental load reflections by a ferrite isolating system 37.

Waveguide means 38, conveniently constituted by a flexible waveguide, connect the radiofrequency modulation means 33 to irradiation means, constituted by a radiating head 32 that comprises an acceleration structure 39 constituted by a plurality of acceleration cavities 26 (also known as resonant cavities) arranged in series one next to the other. The acceleration cavities are connected to each other by vacuum-tight braze welding.

The acceleration cavities 26 of the acceleration structure 39 are designed so as to produce radio-frequency self-focusing along the X-axis of said cavities. Self-focusing has been obtained by using different length values for the first, second, third, fourth and fifth acceleration cavities, so that the lengths increase from the first cavity to the fifth one and are constant for the subsequent cavities. Particularly, it has been found that the optimum lengths for the first, second, third, fourth and fifth cavities are 25 mm, 40 mm, 45 mm, 48 mm and 50 mm, respectively. The energy of the electrons and their capture have also been treated for the first cavity, in which the electrons are not yet relativistic and the values of b and r (Lorenz parameters) vary appreciably.

For an in-depth treatment of radio-frequency self-focusing of electrons, reference should be made to J. Livingood, "Principles of particle accelerators", Argonne National Laboratory, Van Nostrand Company, N.Y., 1961.

A cathode 28 is placed in front of the first acceleration cavity and is supplied by the cathode modulation means 36; a thin titanium lamina is arranged outside the last acceleration cavity for vacuum tightness.

In FIG. 4, the reference numeral 41 designates a particular area of the body of a patient that must be treated by irradiation by means of the apparatus according to the invention.

FIG. 5 is a lateral elevation view of the apparatus according to the invention, in which the reference numeral 50 designates a supporting structure fixed to the floor or resting thereon.

An articulated structure 51 is located on the supporting structure 50 and is meant to support and move the radiating head 32; a diaphragm 60 is applied to said radiating head in the position where the electronic beam exits.

In detail, the articulated structure 51, commonly termed tube support, is constituted by a vertically arranged robot comprising four articulated and mutually interconnected segments designated by the reference numerals 51a, 51b, 51c, and 51d, which allow to arrange the radiating head 32 in any spatial position.

The articulated segments 51a, 51b, 51c, and 51d are mutually pivoted so as to give the radiating head 32 six degrees of freedom in space.

In particular, the articulated segment 51a is rotatable about the rotation axis 52 of the supporting structure 50 both clockwise and counterclockwise; the articulated segment 51b is rotatable in both directions about the hinge axis 53; the segment 51c is rotatable in both directions about the hinge axis 54 as well as about the axis 56; and the segment 51d is rotatable in both directions about the hinge axis 55.

The reference numeral 57 designates a supporting post for an operating table 58. Said post rests on a footing 59 that is moderately shielded, with respect to the floor, only if access to the rooms beneath the operating room is not prohibited during use of the apparatus according to the invention. Said shielding is not necessary otherwise.

Control means, advantageously comprising a movable button panel 61, control the apparatus according to the invention.

Figure 6:
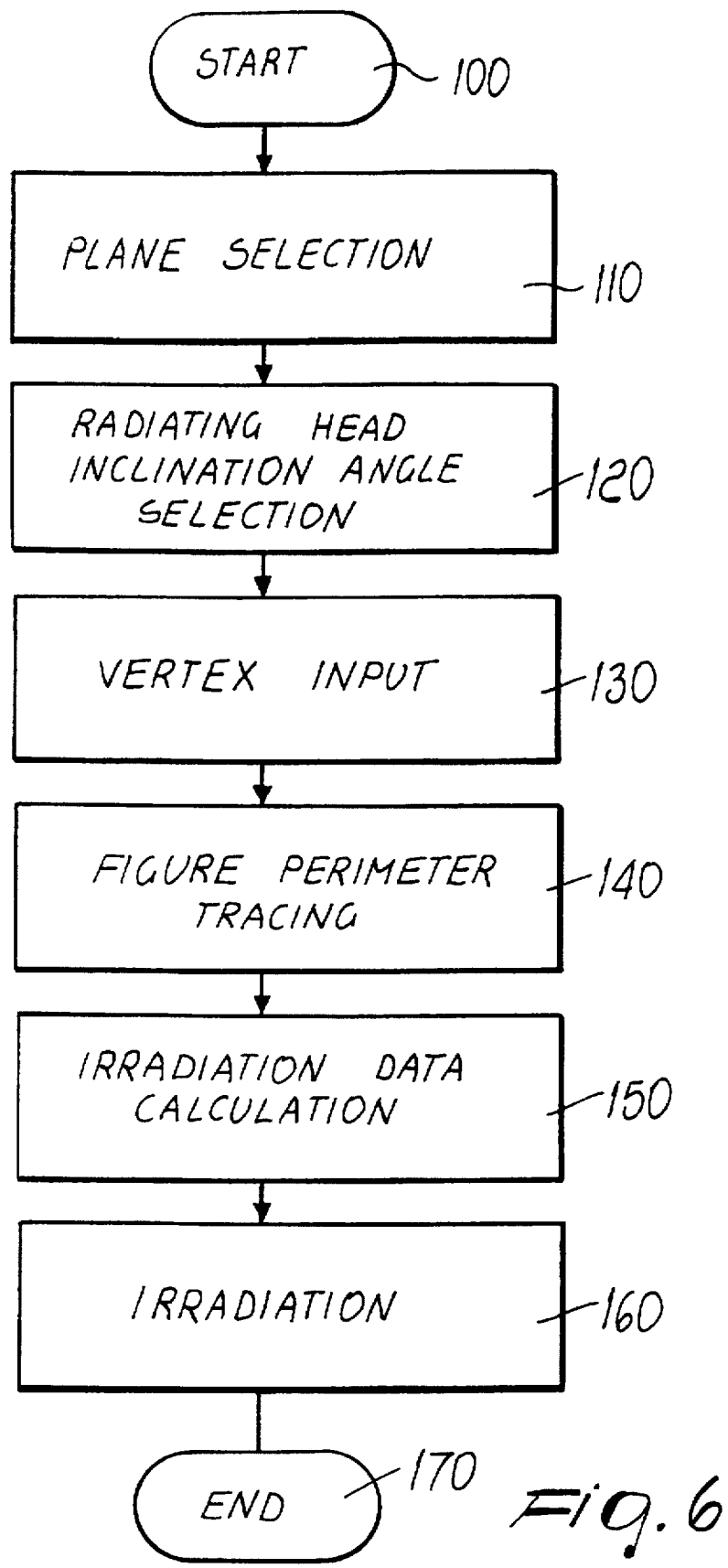
FIG. 6 is a flowchart of the steps for the characterization of an area of the body of a patient to be treated with the apparatus according to the invention.
Figure 7:
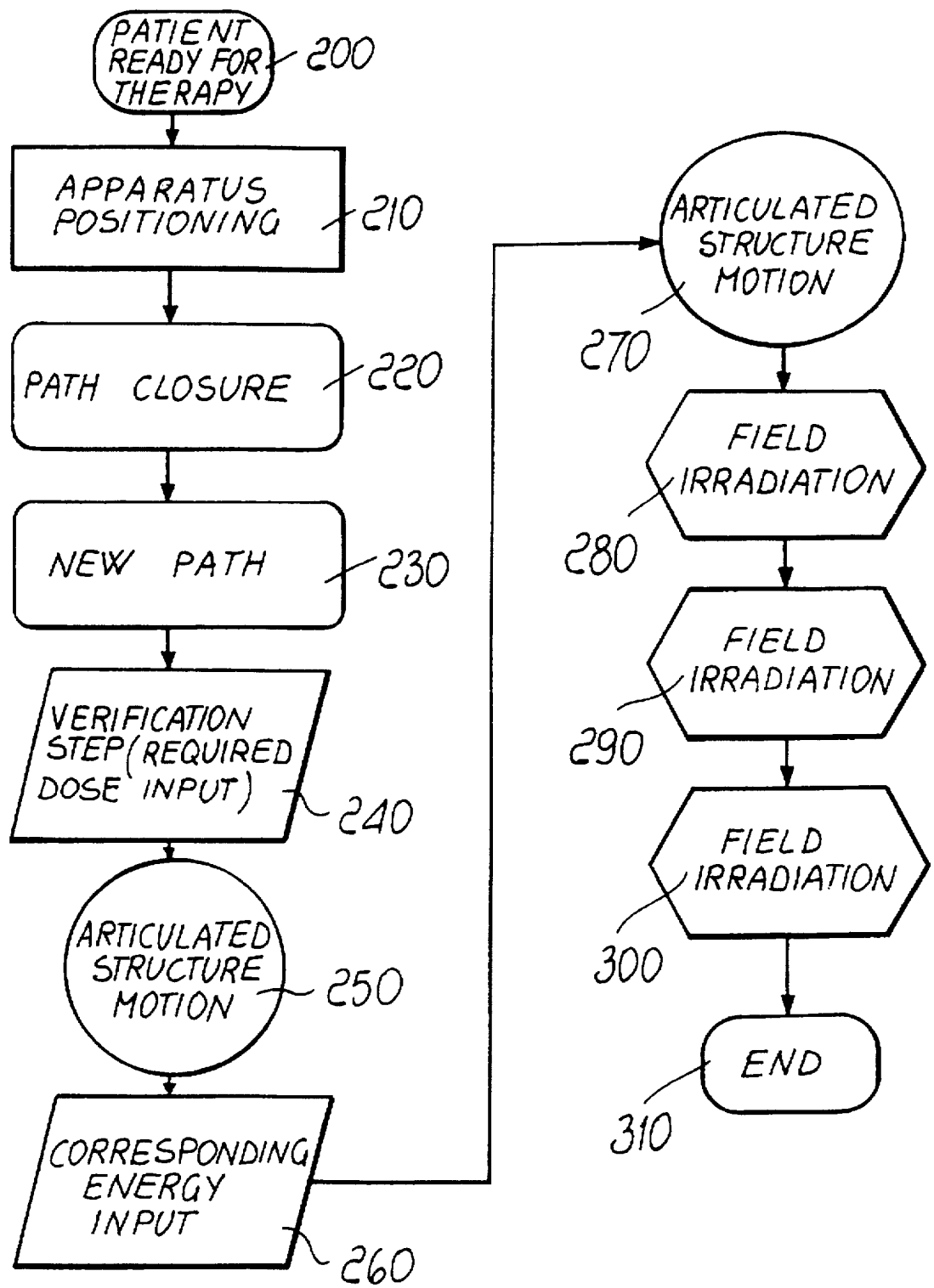
FIG. 7 is a flowchart of the operating steps for scanning irradiation by using the apparatus according to the invention.

FIGS. 6 and 7 are flowcharts of the operating steps of the apparatus according to the invention, which are handled by the processing means 40.

With reference to the above figures, the operation of the apparatus for the linear acceleration of electrons according to the invention is as follows.

The robot constituted by the articulated segments 51a, 51b, 51c, and 51d allows to orientate the radiating head 32 so as to direct the electron beam exactly onto the region where the therapy is to be performed. The possibility of orientating the radiating head 32 allows to avoid expanding the beam and therefore allows precise treatment of the region to be irradiated, bringing the radiating head 32 very close to the region to be irradiated. This, in comparison with the minimum possible distance that can be obtained with known linear accelerators, which varies from 80 to 100 cm, allows the apparatus according to the invention to have a much higher efficiency, since there is no beam scattering and a much lower power level is thus required.

Continuous measurement of the position of the various articulated segments that constitute the robot occurs by means of a sensor system (not shown) with which the robot is equipped.

The processing means 40 allow to predefine the desired movements of the articulated segments 51a14 51d that constitute the robot, and therefore of the radiating head 32, so that said radiating head closely follows the contour of the region to be irradiated; it is furthermore possible to set the desired doses of radiation for each point of the region to be treated.

The modulation means generate and control the radio-frequency and feed to the cathode 28. The generated radio-frequency is sent to the acceleration cavities by means of the flexible waveguide 38.

The electrons that move along the axis of the acceleration cavities 26 are gradually accelerated by the radio-frequency field inside each cavity 26 until they reach the desired final energy. The electrons exit from the acceleration structure 32 through the thin titanium lamina 25, the thickness whereof allows the electrons to pass therethrough without losing an appreciable part of the energy they possess.

The radio-frequency electric field used to accelerate the electrons is produced by the magnetron 35, which feeds the acceleration structure 32 by means of the waveguide 38.

The modulator of the cathode 36 feeds the cathode and synchronizes its operation so that the train of radio-frequency pulses that feeds the acceleration structure 32 is matched by an emission of electrons on the part of the cathode.

The beam of electrons is focused and accelerated simultaneously in the first cavities with a set combination of the cathode injection energy and of the length of the first, second, third, fourth and fifth cavities, and can pass through the center of the subsequent cavities of the acceleration structure after the peak of the radio-frequency, so as to undergo additional focusing.

The beam of electrons is pulsed, and each pulse lasts 4 microseconds. The frequency of the pulses can be fixed or variable.

Use of self-focusing of the electron beam allows to eliminate auxiliary devices used in known accelerators, and in this manner the electron beam does not encounter metallic masses along its path and therefore does not produce radiation, allowing to use the apparatus according to the invention directly in the operating room without particular protective measures.

Use of the processing means 40 allows to use the apparatus according to the invention for mechanical scanning irradiation. The operating procedures required for this scanning irradiation comprise four different operating states of the acceleration apparatus.

These four states are:

instruction step;

learning step;

verification step; and therapy step.

FIG. 6 is a block diagram of the sequence of steps for defining an area to be irradiated, which is called "source plane", performed by the processing means 40; in said figure, after the initial step 100, there is a step 110 for selecting the plane on which the area to be irradiated lies; the step 110 is followed by the step 120 for selecting the inclination angle of the radiating head 32 with respect to the defined source plane; this is then followed by the step 130 for entering the vertices of the figure to be irradiated, the step 140 for tracing the perimeter of the figure for confirmation, the step 150 for calculating the data for irradiation, the irradiation step 160, and finally the end step 170.

With reference now to FIG. 7, when the patient is ready for electron therapy (step 200), the apparatus according to the invention is placed (step 210), by opening the articulated structure 51, so that its beam direction indicator is trained on the center of the area to be treated. This movement is controlled by means of the movable button panel 61.

At this point, the apparatus is placed in the learning state: the operator starts to move the beam over a path that coincides with the edge of the region to be treated; this path is developed over more or less spaced points, depending on the complexity of the profile, and the processing means 40 interpolate and connect the various points with straight segments or circular arcs.

Once the path has been closed (step 220) the operator can start another one (step 230) if the therapy recommends treatment with fields that are differentiated in terms of dose and/or energy; the various fields thus formed can be concentric or separate.

Once learning has ended, the apparatus is placed in the verification step, during which the operator enters (steps 240 and 260), the required dose and the corresponding energy for each field and the articulated structure 51 constantly moves (steps 250 and 270) along the corresponding paths with its light beam.

Once the verification step has ended, the steps for the irradiation of the various fields (steps 280, 290, and 300) occur. These irradiation steps can be followed on the monitor of the processing means 40, which displays data related in real time to the path in progress, the percentage of treatment performed, the dose given, and the remaining dose.

This is followed by the end step 310.

In the case of conventional irradiation, the operator, after moving the radiating head 32 close to the patient, and after setting the desired dose by virtue of the processing means 40, moves the radiating head 32 towards the collimator cone that is used to protect the parts of the patient's body that are not to be irradiated from the electron beam, and begins the irradiation.

In practice it has been observed that the apparatus according to the invention fully achieves the intended aim, since it allows to provide an apparatus for the linear acceleration of electrons that can be used directly in the operating room without particular protective measures. Furthermore, the apparatus according to the invention is much smaller, lighter, and cheaper than similar known apparatuses.

The separation between the radiating head 32 and the modulation means 33, and their connection by means of the flexible waveguide 38, allow to provide an articulated mechanical arm 51 capable of positioning and moving in space the acceleration structure 39 and the radiating head 32 with extreme precision and in a very flexible manner.

Control by means of an appropriately programmed computer 40 allows to set up the movement of the articulated structure 51 so that the beam of electrons treats the entire tumoral mass, no matter how irregular it might be.

The beam self-focusing characteristic, combined with the shape of the acceleration structure 32, make it unnecessary to have auxiliary external devices for regulating the beam (magnets, etcetera), thus allowing a very low X-ray level. This reduction in radiation allows to use the apparatus in operating rooms without particular shielding.

The use of vacuum-tight braze welding to assemble the various acceleration cavities 26 that constitute the acceleration structure 32 allows to eliminate the external vacuum-tight jacket, thus reducing weight and size.

The device thus conceived is susceptible of numerous modifications and variations, all of which are within the scope of the inventive concept.

Thus, for example, since in the apparatus according to the invention the cross-section of the beam remains very small, the current of the beam must in turn be reduced considerably, on penalty of risking the delivery of an excessive local dose and therefore necrotizing the irradiated tissue. The need to reduce the intensity of the current can allow to eliminate the cathode 28 from the acceleration structure 39 by virtue of the known phenomenon of cold extraction of electrons from a metallic material. This phenomenon consists of the fact that an intense electric field applied to a metallic material is able to extract a certain number of electrons from the outermost atomic orbits. The number of electrons that can be extracted, however, is not sufficient for the beam currents required by known accelerators.

Finally, all the details may be replaced with other technically equivalent elements.

In practice, the materials employed, so long as they are compatible with the specific use, as well as the dimensions, may be any according to the requirements and the state of the art.

What is claimed is:

1. An apparatus for the linear acceleration of electrons, comprising:

an articulated structure for moving irradiation means that comprise an acceleration structure constituted by a plurality of cavities;

modulation means for generating, controlling, and transmitting a radio-frequency to said cavities of said acceleration structure; and processing and control means adapted to control said apparatus, said modulation means being separate from said irradiation means, the connection occurring by virtue of waveguide means adapted to carry the radio-frequency to said acceleration structure.

2. An apparatus according to claim 1, wherein said waveguide means comprise a flexible waveguide adapted to connect said modulation means to said irradiation means.

3. An apparatus according to claim 1, wherein said articulated structure comprises a robot for the movement of said irradiation means, said robot being arranged on a supporting structure fixed to the ground.

4. An apparatus according to claim 3, wherein said robot comprises four articulated segments that are movable with respect to each other and allow said irradiation means to move with six degrees of freedom.

5. An apparatus according to claim 1, wherein it comprises processing means adapted to manage said apparatus, said processing means being connected to said modulation means.

6. An apparatus according to claim 1, wherein said plurality of cavities of said acceleration structure are interconnected by means of vacuum-tight braze welds, the cavities from the first to the fifth one having increasing lengths, the subsequent cavities being identical in length, said plurality of cavities producing a self-focusing of the electron beam.

7. An apparatus according to claim 6, wherein said acceleration structure comprises a cathode located in front of said first cavity and a titanium lamina located outside the last cavity.

8. An apparatus according to claim 1, wherein said modulation means comprise a magnetron, a radio-frequency modulator, and a cathode modulator adapted to enable said cathode.

9. An apparatus according to claim 6, wherein said acceleration structure comprises a titanium lamina located outside the last cavity.

10. An apparatus according to claim 1, wherein said modulation means comprise a magnetron and a radio-frequency modulator.

11. A process for performing intraoperative radiation therapy by using the apparatus for the acceleration of electrons defined in claim 1, comprising the steps that consist of an instruction step, a learning step, a verification step, and a therapy step.

12. A process according to claim 11, wherein said instruction step consists in making said apparatus follow manually the perimeters of the areas to be treated; wherein said learning step consists in storing said perimeters on the part of said apparatus; wherein said verification step consists in verifying said paths and in simultaneously entering the parameters that indicate, for each path, doses and energy of the electron beam used for the treatment; and wherein said therapy step consists in performing the irradiation of said defined areas according to said set doses and energy.

* * * * *

UNITED STATES PATENT AND TRADEMARK OFFICE
CERTIFICATE OF CORRECTION

PATENT NO. : 5,635,721
DATED : June 3, 1997
INVENTOR(S) : Bardi Gianluca et al.

It is certified that error appears in the above-indentified patent and that said Letters Patent is hereby corrected as shown below:

Title page, item [54], and Col. 1, line 1;

please change the present title "APPARATUS FOR THE LINER ACCELERATION OF ELECTRONS, PARTICULARLY FOR INTRAOPERATIVE RADIATION THERAPY"

into

--APPARATUS FOR THE LINEAR ACCELERATION OF ELECTRONS, PARTICULARLY FOR INTRAOPERATIVE RADIATION THERAPY.--

Signed and Sealed this

Twenty-sixth Day of August, 1997

*Attest:*

BRUCE LEHMAN

*Attesting Officer*     *Commissioner of Patents and Trademarks*